United States Patent [19]

Heuer et al.

[11] Patent Number: 5,779,776
[45] Date of Patent: Jul. 14, 1998

[54] ROOTING INHIBITORS

[75] Inventors: Lutz Heuer, Dormagen; Heinz-Joachim Rother, Krefeld, both of Germany

[73] Assignee: Bayer Aktiengesellschaft, Leverkusen, Germany

[21] Appl. No.: 860,608

[22] PCT Filed: Dec. 22, 1995

[86] PCT No.: PCT/EP95/05096

§ 371 Date: Jul. 1, 1997

§ 102(e) Date: Jul. 1, 1997

[87] PCT Pub. No.: WO96/20597

PCT Pub. Date: Jul. 11, 1996

[30] Foreign Application Priority Data

Jan. 4, 1995 [DE] Germany ............... 195 00 123.0

[51] Int. Cl.$^6$ ............................................. A01N 37/18
[52] U.S. Cl. .................. 106/18.32; 106/808; 106/823; 106/284.06; 52/741.3; 504/322; 504/338
[58] Field of Search ............... 106/18.32, 284.06, 106/727, 808, 823; 504/322, 338; 52/741.3

[56] References Cited

U.S. PATENT DOCUMENTS 3,231,398  1/1966  Pauli ............................................. 106/16

3,900,308  8/1975  Poignant et al. ............................... 504/338

OTHER PUBLICATIONS

Chemical Abstract No. 66:46215 which is an abstract of Netherlands Patent Specification No. 6602710 (Sep. 1966).

Chemical Abstract No. 73:108607 which is an abstract of Netherlands Patent Specification No. 6816837 (May 1970).

WPIDS Abstract No. 76:28406 which is an abstract of German Patent Specification No. 2,444,821 (Apr. 1976).

WPIDS Abstract No. 76:84008X which is an abstract of Japanese Patent Specification No. 51-106728 (Sep. 1976).

WPIDS Abstract No. 95:346729 which is an abstract of Great Britain Patent Specification No. 2,288,395 (Oct. 1995).

*Primary Examiner*—Anthony Green
*Attorney, Agent, or Firm*—Sprung Kramer Schaeffer & Briscoe

[57] ABSTRACT

The present invention relates to the use of 2-methyl-4-chlorophenoxypropionamides for protecting buildings, building materials and insulation compounds against the penetration of roots into and through them, and to rooting-inhibiting bitumen mixtures, sealants and insulations.

3 Claims, No Drawings

ROOTING INHIBITORS

The present invention relates to the use of 2-methyl-4-chlorophenoxypropionamides for protecting buildings, building materials and insulation compounds against the penetration of roots into and through them, to rooting-inhibiting bitumen mixtures, sealants and insulations and to antifouling finishing.

The penetration of roots through building materials results in undesirable damage to the materials. Plant roots are capable of destroying, in particular, plastic materials such as sealants, roofing materials, but also asphalt. The penetration of roots into seals of sewers and waste-water pipes, into the coverings of flat roofs, into bitumen insulations of pipelines, bridge constructions and hydraulic structures, and the penetration of roots into and through light bitumen roads are generally known problems. Leaks, corrosion, and damage to buildings, roads and pipelines may result.

The addition of root-inhibitory active compounds to building materials is known and described, for example, in F. Hegemann, Abiogene Bitumenadditive [Abiogenic Bitumen Additives], Bitumen-Teere-Asphalte-Peche 24, 105 (1973).

It is furthermore known to use herbicides such as, for example, 2.4-dichlorophenoxy acetic acid, 2.4.5-trichlorophenoxyacetic acid and α-naphthylacetic acid or their salts, amides or esters, for example isooctyl ester or 1-hydroxy-2-butoxyethane esters, furthermore N-isopropylphenylcarbamate and p-chlorophenyldimethylurea as root penetration inhibitors (DE 1 108 833).

There are also described mixtures of condensates of monochloroacetic acid and a variety of o-chlorophenols or o-chlorocresols, which are said to have these properties (see DE 1 109 294).

Finally, it has been disclosed that amides of di- and polyamines with MCPP acid (2-methyl-4-chlorophenoxypropionic acid) inhibit the growth of roots (DE 1 196 115).

Surprisingly, it has now been found that amides of MCPP acid which are derived from the monoamines of the general formula (I)

in which $R^1$ and $R^2$ are identical or different and represent hydrogen or straight-chain $C_1$–$C_{30}$ alkyl, its branched or cyclic isomers or phenyl are highly potent root penetration inhibitors.

Preferred MCPP acid amides are those in which $R^1$ represents methyl, ethyl, n-propyl, i-propyl, n-butyl, i-butyl, s-butyl, t-butyl, n-pentyl, i-pentyl, neo-pentyl, t-pentyl, cyclopentyl, cyclohexyl, cyclooctyl, n-hexyl, n-heptyl, n-octyl, 2-ethylhexyl, n-nonyl, n-decyl, n-undecyl, n-dodecyl, cyclodecyl, n-tetradecyl, n-tridecyl, n-pentadecyl, n-hexadecyl, n-heptadecyl, n-octadecyl, n-nonadecyl, n-eicosyl, n-$C_{22}$, n-$C_{24}$ or their branched structural isomers, or represents phenyl or benzyl, each of which is substituted by $C_{1-10}$, Cl, Br, OH or OMe; and $R^2$ represents hydrogen, or represents methyl, ethyl, n-propyl, i-propyl, n-butyl, i-butyl, s-butyl, t-butyl, n-pentyl, i-pentyl, neo-pentyl, t-pentyl, cyclopentyl, cyclohexyl, cyclooctyl, n-hexyl, n-heptyl, n-octyl, 2-ethylhexyl, n-nonyl, n-decyl, n-undecyl, n-dodecyl, cyclodecyl, n-tetradecyl, n-tridecyl, n-pentadecyl, n-hexadecyl, n-heptadecyl, n-octadecyl, n-nonadecyl, n-eicosyl, n-$C_{22}$, n-$C_{24}$ or their branched structural isomers, or represents phenyl or benzyl, each of which is substituted by $C_{1-14}$, Cl, Br, OH or OMe; or $R^1$, $R^2$ originate from amines derived from renewable raw materials and thus have a natural isomer and chain length distribution, such as, for example, fatty amines, coconut fatty amine, stearyl amine, oleyl amine, dehydroabietyl amine, tallow fatty amine, octyl amine, dodecyl amine, tetradeyl amine, hexadeyl amine, octadecyl amine, distearyl amine, dicocoamine, di-tallow amine, and mixtures of these.

In the case of the branched structural isomers, other alkyl radicals which are preferred are those which can be prepared by means of the Grubert reaction, such as, for example, 2-hexyldecanol (Isofol 16), 2-butyloctanol (Isofol 12), 2-decyltetradecanol (Isofol 24), 2-octyldodecanol (Isofo 20) and other Isofols (by Condea, Brunsbüttel) from 10 to 30, or mixtures of these which are Aminir in a subsequent reaction step.

Especially preferred amongst these amides are those of the amines of the formula (I) in which $R^1$ represents n-decyl, n-dodecyl, n-tridecyl-, n-tetradecyl or their branched structural isomers and $R^2$ represents H or the above mentioned amides which are derived from renewable raw materials, for example coconut fatty amine.

All MCPP acid amide isomers and racemic and optically active MCPP acid amides are used according to the invention. The amides can be used singly or in combination with each other. For the purposes of rooting-inhibiting finishing, the amides are mixed directly in the form of solutions or other preparations such as, for example, with bitumen or coal tar pitches with the building materials or insulation compounds. Exemplary and preferred sealants are described, for example, in WO 92/10537. This also applies to bitumen emulsions in which the amides claimed are preferably employed. The same is true analogously for corresponding amides which are derived from 2,4- dichlorophenoxyacetic acid.

The normal use concentrations of the MCPP acid amides are 0.2 to 5% by weight based on bitumen.

The amides can be prepared by known methods (see, for example, Organikum [Organic Chemistry], Deutscher Verlag der Wissenschaften 1990) and can generally be obtained in pure form by distillation, rectification, crystallization, zone melting or kugelrohr distillation. If the amides can no longer be distilled, they are to be purified by chromatography on silica gel. The pure amides contain less than 0.8 % MCPP acid, technical-grade qualities less than 2 % MCPP acid.

The following amides were tested for their protective action against root penetration in accordance with DIN 4062. Their leaching behaviour from bitumen was also studied. The latter provides information about the period within which the compound is present in bitumen in active form (test: 0.8 % of active ingredient based on bitumen weight, contact area 280 cm$^2$, 1 l water, 25°C., water change every 4 weeks, analyte: MCPP acid in mg/l).

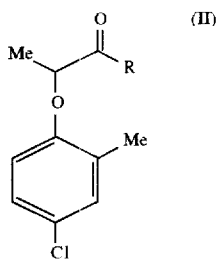

(II)

| R | Test for rooting inhibition in accordance with DIN 4062 | 12th-week water treatment (leaching behaviour) |
|---|---|---|
| —NH—cyclohexyl | ≧0.8% no root penetration through the test material. | Σ 3.5 mg/l of MCPP |
| —NH-$^nC_{12}H_{25}$ | ≧0.8% no root penetration through the test material. | Σ < 2 mg/l of MCPP |
| —NH-coconut fat (coconut fatty amine) | ≧0.8% no root penetration through the test material. | — |
| Comparison experiment —O—(CH$_2$CH$_2$—O)$_Q$- | ≧0.8% no root penetration through the test material. | Σ < 13.5 mg/l of MCPP |
| Comparison experiment (sedimentation example) —NH—C$_6$H$_{12}$—NH— | ≧0.8% root penetration through the test material | — |
| Comparison experiment (sedimentation example) —NH—C$_2$H$_4$—N(—C$_2$H$_4$—NH—)— | ≧0.8% root penetration through the test material | — |

Q = 1 to 10, mean molecular weight ~ 200

Thus, in accordance with DIN 4062, amides from monoamines of the formula (I) are clearly superior to the di and triamides, but do not perform less well than the esters of polyalcohols and, due to their chemical/physical properties, are easier to handle from the technological point of view, in comparison with the polyglycol diol diesters. Since, moreover, the amides claimed contain less MCPP acid than the diesters, based on their molecular weight, they are superior to the latter in terms of activity per acid group. This superiority is also expressed clearly in the free MCPP acid found in the leaching test.

We claim:

1. A method of protecting a building, a building material or a building insulation against the penetration of roots into and through said building, building material or building insulation, said method comprising treating said building, building material or building insulation with an amount of a compound which is effective to inhibit said root penetration, said compound having the formula (IIa):

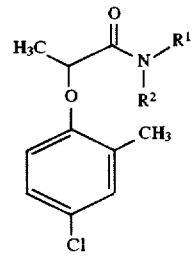

(IIa)

wherein

R$^1$ and R$^2$ are identical or different and are selected from the group consisting of hydrogen and straight-chain, branched or cyclic alkyl having 1 to 30 carbon atoms.

2. A building material or building insulation comprising a root penetration-inhibiting effective amount of a compound of the formula (IIa):

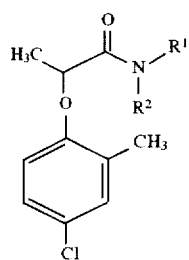 (IIa)

wherein

R[1] and R[2] are identical or different and are selected from the group consisting of hydrogen and straight-chain, branched or cyclic alkyl having 1 to 30 carbon atoms.

3. A bitumen-containing substance comprising a root penetration-inhibiting effective amount of a compound of the formula (IIa):

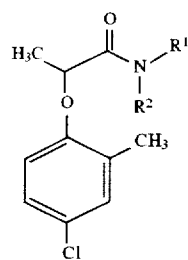 (IIa)

wherein

R[1] and R[2] are identical or different and are selected from the group consisting of hydrogen and straight-chain, branched or cyclic alkyl having 1 to 30 carbon atoms.

* * * * *